United States Patent [19]

Ryan

[11] 4,372,941

[45] Feb. 8, 1983

[54] NOVEL RADIOASSAY PROCEDURE

[76] Inventor: James W. Ryan, 3420 Poinciana Ave., Dade County, Miami, Fla. 33133

[21] Appl. No.: 184,653

[22] Filed: Sep. 5, 1980

[51] Int. Cl.$^3$ ............................................. A61K 43/00
[52] U.S. Cl. ....................................................... 424/1
[58] Field of Search ................. 424/1, 12; 435/15, 24, 435/26

[56] References Cited

U.S. PATENT DOCUMENTS 4,115,374  5/1978  Ryan et al. .................... 260/112.5 R

OTHER PUBLICATIONS

Ryan et al., Biochem. J. 120, 221-223, (1970).
Friedland et al., Am. J. Clin. Path. 66, 416-424, (1976).
Piquilloud et al., Biochem. Biophys. Acta. 206, 136-142, (1970).
Dipierre et al., Enzyme 19, 65-70, (1975).
Dorer et al., Biochem. Biophys. Acta. 429, 220-228, (1976).
Cushman et al., Biochem. Pharmac. 20, 1637-1648, (1971).
Rorhbach, Anal. Biochem. 84, 272-276.
Ryan et al., Tissue and Cell 10, 555-562, (1978).
Glenner et al., Nature 194, 867-876, (1962).
Conroy et al., Anal. Biochem. 87, 556-561, (1978).
Nobel et al., IRCS Med. Sci. 7, 540-542, (1979).
Fonnum, Biochem. J. 115, 465-472, (1969).
Beavan et al., Clin. Chim. Acta. 32, 67-73, (1971).
Sankaran et al., Anal. Biochem. 54, 146-152, (1973).
Bigl, Acta. Biol. et. Med. Germ. 34, 1437-1440, (1975).
Dixon et al., Clin. Chem. 22, 1746-1747, (1976).
Mokrasch, Anal. Biochem. 75, 336-339, (1976).
Joiner et al., J. Immunol. Methods, 31, 283-290, (1971).
Weinshilboum et al., Clin. Chim. Acta. 97, 59-71, (1979).
Leaback et al., Anal. Biochem. 106, 314-321, (1980).
DeJong et al., Anal. Biochem. 106, 397-401, (1980).

*Primary Examiner*—Leland A. Sebastian

[57] ABSTRACT

A rapid, efficient and accurate method is provided for quantitatively assaying for an enzyme, such as angiotensin converting enzyme, an aminopeptidase, a carboxypeptidase, or trypsin, which catalyzes hydrolysis of a radiolabelled substrate to produce a radiolabelled remnant product preferentially soluble in a water-immiscible organic solvent, whereby the assay is conducted in a vial having a volume of not more than 20 milliliters, preferably 7 ml. or less, by incubating substrate in buffer and sample, stopping the reaction after a predetermined time with, e.g., acid or base, adding the water-immiscible organic solvent containing scintillant, capping the vial, mixing by inverting the vial whereupon a spontaneous phase separation occurs. The radioactivity of the organic phase is then counted in an appropriate scintillation counter and the enzymic activity is thereupon calculated.

23 Claims, No Drawings ethyl acetate extract is mixed with toluene based scintillation fluid, followed by scintillation counting in an appropriate device.

In U.S. Pat. No. 4,115,374, J. W. Ryan and A. Chung have disclosed a method wherein an acylated tripeptide substrate which may be labelled radiometrically, colorimetrically or fluorimetrically is hydrolyzed to a remnant product that is extracted, after stopping the hydrolytic reaction, into a suitable solvent by rotary agitation and centrifugation. When radiolabelled remnant is used, ethyl acetate is the solvent and the layer containing the remnant product separates as the upper phase. Aliquots of this layer are mixed with toluene based scintillation fluid and subjected to appropriate measurement. Preferred substrates are, e.g., [$^3$H]Hip-Gly-Gly, [$^{125}$I-parahydoxyphenylpropionyl]-Gly-Gly-Gly and [$^3$H-benzoyl]-ProPheArg, depending upon the type of sample to be assayed. See also Ryan, J. W., Chung, A., Martin, L. C. and Ryan, U. S., Tissue and Cell, 10, 555 (1978).

The aminopeptidase enzymes are characterized by their ability to hydrolyze a peptide or protein at the N-terminal amino acid. Their substrate specificity varies from enzyme to enzyme. Aminopeptidase A, first isolated by Glenner, G. G., McMillan, P. J. and Folk, J. E., Nature, 194, 867 (1962) preferentially removes N-terminal dicarboxylic acids, is activated by $Ca^{++}$ and inhibited by EDTA. A known assay for aminopeptidase A involves the use of α-aspartylnaphthylamide as a substrate, whereby the hydrolysis products are aspartic acid and the naturally fluorescent naphthylamine.

The carboxypeptidase enzymes are characterized by the ability to hydrolyze proteins or peptides at the C terminal amino acid. Known assays for carboxypeptidases are of the general type of the Cushman and Cheung ACE assay, discussed supra, whereby a hippuric acid remnant is obtained by hydrolysis of a substrate such as HipArg and measured as described above, in a spectrophotometric method.

SUMMARY OF THE INVENTION

The present invention is based upon the discovery that assays for various enzymes may be performed with greater efficiency, precision, speed and accuracy by selecting appropriate radiolabelled substrates which hydrolyze to provide radiolabelled remnants extractable in organic solvents and assaying under conditions such that the entire assay is performed in a single disposable vessel of a volume in the order of less than 20 ml. and preferably 7 ml. or less.

The technique is of special applicability to assays for ACE, aminopeptidases and carboxypeptidases and may also be used in other assays that produce or may be designed to produce an organic solvent-soluble labelled remnant product. It eliminates the need for transfers of radiolabelled products formed in the assay from vial to vial. It provides a measure of whole sample activity and decreases possibilities for error consequent from measurement of aliquots. It vitiates the need for centrifugation and vortexing. It cuts down on assay time and on the volume of radioactive waste product produced in similar radioimmunoassays in current use. In its ACE embodiments, it constitutes an improvement upon the procedures disclosed in U.S. Pat. No. 4,115,374.

The described method is of particular advantage in a clinic or doctor's office where a short assay time, the ability to work with a small sample of serum or other physiological material and the minimization of radioactive waste production are primary considerations. It is equally applicable in research laboratories because of its convenience and reliability.

In its preferred embodiments, the assay procedure of this invention involves incubating substrate and sample (containing the enzyme to be assayed for) in buffer in a vial having a volume of 20 ml. or less, stopping the reaction with an appropriate inhibitor, such as an acid or base, in an appropriate organic solvent or solvent mixture containing scintillant, capping the vial, inverting several times whereby extraction, followed by spontaneous organic—aqueous phase separation occurs and counting the radioactivity of the organic phase in an appropriate scintillation counter.

For reasons that are not clearly understood, tritiated benzylamide-containing substrates in general require a modified procedure wherein a measured portion of the organic phases must be removed from the reaction vial to permit accurate counting. This phenomenon, however, does not occur when Asp [$^3$H] benzylamide is used in the procedure of this invention as substrate for aminopeptidase A.

The substrates of this invention are water soluble organic solvent-insoluble, radiolabelled peptides and modified peptides so selected that their hydrolysis by the enzyme to be assayed for will produce an organic solvent-soluble remnant product containing the radiolabel, which remnant product is preferentially extractable from aqueous solution with the organic solvent or solvent mixture.

DETAILED DESCRIPTION OF THE INVENTION

The present invention rests upon the discovery that assays for enzymes which preferentially catalyze hydrolysis of radiolabelled substrates to produce radiolabelled remnant products capable of selective extraction into a water-immiscible organic solvent or solvent mixture may be performed with greater ease, more accurately and more reproducibly than in the past on a "minivial" or "microvial" scale involving a total reactant volume below 20 ml. and preferably below 7 ml. In some embodiments assays in vials of 2 ml. have produced highly satisfactory results. Beem capsules of even smaller volumes have also been used for assays of this invention with satisfactory results.

Enzymes that may be assayed for in the procedures of this invention include ACE, aminopeptidases including aminopeptidase A, carboxypeptidases, trypsin, etc.

When ACE is the enzyme to be assayed for, radiolabelled HipGlyGly, HipHisLeu, benzoyl-Gly-His-Leu or benzoyl-Pro-Phe-Arg are useful in this invention. The radiolabel is preferably tritium but may be $^{14}$C, $^{125}$I, $^{131}$I or another of the well known radiolabel elements. When the substrate is benzoyl-Pro-Phe-Arg care should be taken that the sample to be assayed is not a urine sample since carboxypeptidase N contained in urine competes with ACE in hydrolyzing the substrate to produce nonspecific results.

The present method of assay is especially suitable, with the caveat given, for the assay of ACE in samples of clinical material, serum, urine and the like. When the ACE in a serum sample is to be assayed, it is necessary to obtain non-hemolyzed blood, because the presence of hemoglobin in the serum reduces the efficiency of scintillation counting in a manner which is difficult to compensate for.

NOVEL RADIOASSAY PROCEDURE

BACKGROUND OF THE INVENTION

Elucidation of the roles of various enzymes in both normal and abnormal physiological states has led to an increasing demand for convenient, rapid and reliable techniques of assaying for specific enzymes. Such assays are valuable tools in diagnosis, in monitoring effectiveness of drugs and other pharmacological agents and in the further study of the enzymes per se, their capabilities and their physiological effects.

The need for rapid, reliable and precise assays for enzymes indigenous to the renin-angiotensin system has grown as more has been learned about the part which the system and its individual enzymes play in the regulation of blood pressure, and the ways in which inhibitors of specific enzymes present in the system may aid in such regulation.

Presently known assays for such enzymes are in most instances inefficient, procedurally cumbersome and timeconsuming, requiring many manipulative steps which may adversely effect the precision and accuracy of the results. Those which depend upon the use of radioactive tags such as $^{14}C$ or $^{3}H$ are frequently disadvantageous because of current problems in disposing of radioactive waste; those which depend upon non-radioactive fluorescent or colorimetric tags are frequently low in sensitivity and, hence, are wanting in precision and accuracy.

Throughout the specification, the following symbols have the significance shown in the table:

TABLE 1

| | | |
|---|---|---|
| Ala | = | L-alanine |
| Arg | = | L-arginine |
| Asp | = | L-aspartic acid |
| Gln | = | L-glutamine |
| <Glu | = | pyro-L-glutamic acid |
| Gly | = | glycine |
| Hip | = | Hippuric acid (Benzoyl glycine) |
| His | = | L-histidine |
| Ile | = | L-isoleucine |
| Leu | = | L-leucine |
| Lys | = | L-lysine |
| Phe | = | L-phenylalanine |
| Pro | = | L-proline |
| Ser | = | L-serine |
| Trp | = | L-tryptophan |
| Tyr | = | L-tyrosine |
| Val | = | L-valine |
| ACE | = | Angiotensin converting enzyme |
| Bicine | = | N,N—bis (2-hydroxyethyl) glycine |
| EDTA | = | Ethylene diamine tetraacetic acid |
| Hepes | = | N—2-hydroxyethylpiperazine-N'—2-ethanesulfonic acid |
| HPP | = | p-hydroxyphenylpropionyl |

DESCRIPTION OF THE PRIOR ART

Angiotensin converting enzyme (ACE), carboxypeptidase B and aminopeptidase A activities have all been measured in prior art assay procedures.

Known methods for measuring ACE depend upon the reactivity of the enzyme with a substrate, especially of the class of acylated tripeptides and larger polypeptides having an unblocked carboxyl group. ACE is itself of a peptidyldipeptide hydrolase, and it acts to catalyze the hydrolysis of the penultimate peptide bond at the C-terminal end of the aforementioned class of tripeptides and larger polypeptides according to the diagrammatic reaction $$R - A_2 - A_1 + H_2O \xrightarrow{ACE} R - OH + H - A_2 - A_1,$$

wherein
$A_1$ = an amino acid at the carboxyl terminus of a peptide
$A_2$ = an amino acid linked to $A_1$ by a peptide bond and R = an N-substituted amino acid linked to $A_2$ by a peptide bond. In the known assays, either the remnant product $R_1OH$ or the dipeptide cleavage product $HA_2A$, contains a tag which may be a radiolabel, a fluorescent label or a colorimetric label, and the tagged product is separated from the reaction mixture by some means in order to permit its measurement in a suitable apparatus.

Known methods for measuring the dipeptide reaction product include:

(a) That described by Ryan, J. W., Stewart, J. M., Leary, W. P. and Ledingham, J. in Biochem. J. 120, 221 (1970) wherein angiotensin I labelled with $^{14}C$ or $^{3}H$ in the carboxy terminal moiety was used as substrate. The procedure involved multiple extractions and centrifugations. The labelled dipeptide product was separated from the substrate by gel filtration or ion exchange chromatography and placed in a solution of Omnifluor (0.4% w/v) in toluene for radioactivity counting.

(b) The acylated tripeptide HipHisLeu was used as substrate and its dipeptide cleavage product was reacted with the reagent O-phthaldialdehyde to form a fluorescent adduct. The procedure requires two incubations, one of sample with substrate in buffer which is stopped with NaOH after 15 minutes and one of adduct with HCl of 30 to 90 minutes, which involves a centrifugation of 10 minutes followed by standing. The fluorescence intensity as a function of HisLeu concentration is nonlinear and a standard curve is required in order to interpret the results. Friedland, J. and Silverstein, E, Am.J.Clin.Path. 66, 416 (1976); see also Piquilloud, Y., Reinharz, A. and Roth, M. R., Biochim. Biophys. Acta, 206 136 (1970); Depierre, D. and Roth, M., Enzyme, 19, 65 (1975).

(c) The acylated tripeptide HipGlyGly was used as substrate and its dipeptide reaction product GlyGly was measured by the renhydrin color reaction using an automatic analyzer. See Dorer, F. E., Kahn, J. R., Lentz, K. E., Levin, M. and Skeggs L. T., Biochim. Biophys. Acta, 429, 220 (1976).

Several methods for measuring the remnant product are also known. Cushman, D. W. and Cheung, H. S., Biochem. Pharmac 20, 1637 (1971) described a method employing HipHisLeu as substrate wherein remnant hippuric acid is extracted with ethyl acetate after a 30 minute incubation of substrate and sample in buffer, stopped with HCl. The extraction removes only about 91% of the remnant product. The ethyl acetate must then be removed by evaporation and the hippuric acid remnant must thereupon be redissolved in aqueous medium and measured spectrophotometrically at 228 nm. This assay is complicated by large absorbance blanks due to frequent presence of compounds soluble in ethyl acetate and absorbant at 228 nm. Accordingly, Rohrbach, M. S., Anal. Biochem. 84, 272 (1978) has proposed a modification wherein the substrate is [glycine-1-$^{14}C$]-Hip-His-Leu and the remnant product is [glycine-1-$^{14}C$] hippuric acid. In this procedure, the labelled remnant product is extracted into ethyl acetate with vigorous vortexing and centrifuging, and an aliquot of Reaction conditions optimal for carrying out an ACE catalyzed hydrolysis of a substrate of the present invention are the same as have been previously described in the art. Detailed studies of optimal conditions using HipGlyGly as substrate have been reported by Dorer, et al. The pH optimum is approximately 8.0 although greater than 50% maximal activity is obtained in the pH range of 7.0-9.0. Hydrolysis of either HipGlyGly or HipHisLeu by ACE requires chloride ions. Buffer composition significantly affects enzyme activity. Phosphate is inhibitory. Hepes buffer (N-2-hydroxyethylpiperazine-N'-2-ethanesulfonic acid) is preferred because it provides maximum activity. Preferred conditions of buffer composition, ionic strength pH, and temperature are described in Example 1.

The present invention is more rapid and sensitive and simpler procedurally than those known for ACE in the art. The entire assay procedure is conducted using a single vessel (2-20 ml. scintillation vial or Beem capsule) for the incubation, extraction and liquid scintillation counting.

By the present invention, serum diluted in assay buffer is mixed with buffered radiolabelled substrate, and the resulting reaction mixture is incubated at 25°-37° C. for 5-30 minutes in the liquid scintillation vial or Beem capsule. The volume of the reactants can be varied according to the volume of the organic extraction solvent to be used. Thus, 50 µl of serum diluted in buffer (diluted 1/5-1/100 according to the choice of substrate and length of incubation to be used) can be incubated in a 2 ml. scintillation vial with 50 µl of buffered substrate. The reaction can be stopped by adding 50 µl of 0.5 N HCl. The radiolabelled remnant product is separated from unhydrolyzed substrate by adding 1500 µl of an organic solvent or organic solvent mixture compatible with liquid scintillation counting [e.g. toluene/ethyl acetate, (2:1 by vol)]. By including a scintillator or mixture of scintillators (e.g. POPOP/PPO, Omnifluor, or terphenyl) that is soluble in the organic solvent but not in the acid aqueous solution, the radioactivity of the organic phase can quantified by liquid scintillation counting whereas the radioactivity of the aqueous phase is not counted and does not contribute significantly to the scintillation of the organic phase. Thus, following extraction and phase separation (the latter occurs spontaneously and does not require centrifugation), the scintillation vials can be submitted immediately for counting.

So long as volumes of the reactants and the extraction solution remain proportional, similar results can be obtained by scaling-up or scaling-down. For example, the same reaction can be conducted in a 7 ml. scintillation vial by incubating 100 µl of diluted serum with 100 µl of buffered substrate. The reaction is stopped with 100 µl of the acid and then extraction is effected by mixing the above with 3,000 µl of the organic phase containing a scintillator. After the scintillation vial is capped, mixing can be accomplished by simple inversion.

The proportions of reaction mixture, stop solution and extraction solution can be varied over a wide range and still produce a valid assay provided that the computation of results takes into account changes in the relative extractability of a given substrate and its remnant product. The extraction of the remnant product (and separately and independently, the extraction of substrate) is a function of its relative solubility in the solvents of the upper and lower phase. Further, the exact fraction of a substance extracted is also a function of relative volumes of upper and lower phases. In the preferred method, the volume of the upper phase is ten times that of the lower phase when the upper phase is toluene/ethyl acetate (2:1 by vol). However, as the quantity of toluene is increased in respect to ethyl acetate, the proportional volume of upper phase to lower phase must be increased to obtain the same fractional extraction of remnant product. Alternatively, the computation of enzymic activity must be modified to reflect a different fractional extraction of product. Conversely, as the volume of ethyl acetate is increased in respect to toluene, it becomes possible to use a smaller volume of upper phase to extract product with the same efficiency. The partition coefficient (relative solubility) of substrate changes independently and must also be assessed. Further, as the relative abundance of toluene falls, the solubility of a scintillator such as terphenyl also falls.

By conducting the reaction, extraction and quantification procedures in one vessel, the amount of time required for the assay is greatly reduced. In addition, in the previous radioassay procedure, radioactivity is left in two vessels: the reaction tube and the scintillation vial, thus doubling the number of items designated for radioactive waste disposal. Pipette tips used for transferring radioactive material from the reaction tube to the scintillation vial add to the problem of disposal of radioactive waste.

For weak $\beta$-emitters such as $^3H$ or $^{14}C$ used in relatively small quantity, the major consideration in radioactive waste disposal is volume, not radioactivity per se. At present, none of the government-approved radioactive dumping grounds are receiving radioactive waste. Consequently, laboratories must store their own bulk radioactive waste for an indefinite, long period. The present invention more than halves the volume and numbers of items that must be thus stored.

A further advantage of the present invention is sensitivity of assay. In the radioassay of U.S. Pat. No. 4,115,374, a fraction, usually half, of the organic phase was transferred to a scintillation vial for counting. In the present invention, the radioactivity of the entire organic phase is measured, thus providing twice the distinction between enzyme formed organic-extractable radioactivity and background radioactivity. Further, in the prior technique, remnant product was extracted into ethyl acetate alone, with no admixture of toluene. Under the latter conditions, >6% of the substrate entered the ethyl acetate layer and thereby gave undesirably high background c.p.m. In the present invention, less than 2% of substrate enters the organic phase. Thus, there is greatly improved basis for distinguishing ACE-catalyzed reactions from background.

When enzymes other than ACE are to be assayed for, the method is modified in an appropriate manner. For example, for aminopeptidases and especially aminopeptidase A, Asp[$^3H$] benzylamide is a preferred substrate and the stop solution is 0.5 N NaOH. For carboxypeptidases such as carboxypeptidase N, [$^3H$]benzoyl-Phe-Arg is a preferred substrate, the stop solution is 0.5 N HCl and the extractant is toluene alone, without ethyl acetate.

In certain assays within the scope of this invention it is contemplated that other lower alkyl acetates may be substituted for ethyl acetate. Solvents such as dioxane or water immiscible ethers may be used in some assays. In some instances xylene or benzene may substitute for toluene.

Significantly, when tritiated benzylamides other than Asp[³H] benzylamide are used as substrates, e.g. for trypsin, it has been found that the presence of the unreacted radioactive substrate interferes with accurate counting of the extracted labelled remnant product. This is avoided by removing a measured aliquot of the organic phase containing labelled remnant product from the reaction vial and counting it separately. This may desirably be done in a sealed disposable micropipette tip placed in a clean 7 ml. minivial; in this instance radioactivity contamination of the latter minivial is avoided and only the pipette tip need be consigned to radioactive waste storage.

To date, it has been found that certain known substrates are not amenable to the process of this invention. For example, radiolabelled BzPheAlaPro, a very effective ACE substrate as disclosed in copending U.S. application Ser. No. 854,538 of J. W. Ryan and A. Chung, filed Nov. 25, 1977, is not a satisfactory substrate in the present invention.

A desirable feature of this invention consequent from its vitiation of the need for centrifugation or vortex mixing is avoidance of the stable emulsions which milky appearing serum or other samples containing excess lipids have sometimes formed. These emulsions interfere with a satisfactory assay; they do not form on simple mixing by inversion such as is practiced according to this invention.

It will readily be apparent that, depending upon the enzyme, to be assayed, other substrates with other remnant products than those named herein may be utilized within the scope of this invention. Also clearly, other stop solutions and organic solvents or solvent mixtures can be substituted for those specifically named without departing from the invention.

The ensuing examples are accordingly presented as illustrative rather than limiting of the present invention.

EXAMPLE 1

Preparation of human urinary angiotensin converting enzyme, aminopeptidase A, carboxypeptidase N and kallikrein A volume of two liters of fresh human urine was reduced to approximately 10 ml. by ultrafiltration using an ultrafilter having a retention limit of 10,000 MW. The retentate was chromatographed on a column (2.5×110 cm) of Sephacryl S-200® (Pharmacia Fine Chemicals, Piscataway, N.J.) equilibrated with 0.05 M Tris-HCl buffer, pH 8.0, containing 0.5 M NaCl. The column was developed with the same buffer, and 3.5 ml. fractions were collected. Angiotensin converting enzyme was eluted just behind the void volume ($V_o$) at a ratio of $V_e/V_o$ ($V_e$=volume of elution to the peak of the enzymic activity) of 1.1. The aminopeptidase A and carboxypeptidase N were eluted in overlapping peaks ($V_e/V_o$=1.18). Kallikrein was eluted last ($V_e/V_o$=1.42).

EXAMPLE 2

Assay of human urinary carboxypeptidase N using [³H]benzoyl-Phe-Arg as substrate The partially-purified carboxypeptidase N of Example 1 was dissolved in 0.05 M Tris-HCl buffer, pH 8.0, plus 0.5 M NaCl. Substrate, [³H]benzoyl-Phe-Arg, was dissolved in the same buffer to give a concentration of 130,000 c.p.m./50 μl (76 nM). For the test samples (T), 50 μl of enzyme was added to a 2 ml. scintillation vial containing 50 μl of substrate. Blanks (B) were prepared by adding 50 μl of buffer to a 2 ml. vial containing 50 μl of substrate. The vials were incubated at 37° C. for 3' minutes and then the reactions were stopped by adding 50 μl of 0.2 N HCl. To each vial was added 1.5 ml. of toluene containing Omnifluor, 4 g/liter. The vials were capped and their contents mixed by 30 inversions/vial. After spontaneous separation of the solvent phases, radioactivity was measured by liquid scintillation counting. The radioactivity of total substrate vial ($S_o$) was measured by adding 50 μl of substrate to 10 ml. of RIA-fluor in a 20 ml. scintillation vial. Enzyme activity [E] was computed as follows:

$$[E]/ml. = \frac{\frac{T-B}{S_o} \times 100}{30 \text{ min.} \times 0.05 \text{ ml.}}$$

[E], T, B and $S_o$ are defined above. The factor 100 is to convert fractional substrate utilization into percentage. The factor 30 min. is the time of incubation and 0.05 ml. is the quantity of enzyme in a given test vial. [E] is in units defined such that one unit is the quantity of enzyme required to hydrolyze substrate at a rate of 1% per minute at 37° C.

| Vial | c.p.m. | [E]/ml. |
|------|--------|---------|
| B | 5201 | 0 |
| B | 5176 | 0 |
| T | 17826 | 6.34 |
| T | 18003 | 6.43 |
| T | 17790 | 6.32 |
| T | 17567 | 6.21 |
| T | 17621 | 6.24 |
| T | 17499 | 6.18 |
| $S_o$ | 132,890 | (total substrate) |

EXAMPLE 3

Assay of human urinary aminopeptidase A using α-Asp-[³H]benzylamide as substrate The partially-purified human urinary aminopeptidase A of Example 1 was dissolved in 0.05 M Tris-HCl buffer, pH 8.0, containing 0.5 M NaCl and 0.005 M CaCl$_2$. Substrate, α-Asp-[³H]benzylamide, was dissolved in the same buffer to give a concentration of 89,000 c.p.m./50 μl (approximately 54 nM). Reaction mixtures were prepared in 2 ml. scintillation vials as described in Example 2 for test samples (T) and blanks (B). Substrate ($S_o$) was measured as described for [³H]benzoyl-Phe-Arg of Example 2. The reaction mixtures were incubated at 37° C. for 30 minutes and then reactions were stopped by adding 50 μl of 0.2 M NaOH to each vial. Each of the resulting solutions was mixed with 1.5 ml. of toluene containing Omnifluor, 4 g/liter. The capped vials were submitted for liquid scintillation counting. Enzymic activities ([E]/ml. of enzyme solution) were computed as described in Example 2.

| Vial | c.p.m. | [E]/ml. |
|------|--------|---------|
| B | 2120 | 0 |
| B | 2105 | 0 |
| T | 6007 | 2.92 |
| T | 6101 | 2.99 |
| T | 5988 | 2.91 |
| T | 5900 | 2.84 |
| $S_o$ | 88,788 | (total substrate) |

EXAMPLE 4

Assay of an inhibitor of angiotensin converting enzyme using a standard quantity of enzyme and [³H]hippuryl-His-Leu as substrate Human urinary angiotensin converting enzyme from Example 1 was dissolved in 0.05 M Hepes buffer, pH 8.0, containing 0.1 M NaCl plus 0.75 M Na₂SO₄. The enzyme was diluted in the same buffer such that 100 μl of the enzyme dilution mixed with 100 μl of [³H]hippuryl-His-Leu (in the same buffer at 164,000 c.p.m./100 μl) would, on incubation at 37° C., yield a hydrolysis rate of 8%/15 min. An inhibitor of angiotensin converting enzyme, 3-D-mercapto-2-methylpropanoyl-L-proline, was dissolved in the buffer to give an initial concentration of 1 mg/ml. Eight serial 1:11 dilutions of the inhibitor were made using the same buffer (100 μl of a given solution plus 1,000 μl of buffer to make the next dilution in sequence). Assays were performed in replicate. To a 7 ml. scintillation vial, containing 100 μl of buffered substrate, was added 25 μl of a given dilution of inhibitor. Blank vials and control vials received 25 μl of buffer in each vial and then 100 μl of enzyme was added to each test vial. Buffer, 100 μl, was substituted for enzyme in the blank vials. The vials were incubated at 37° C. for 15 minutes. The reactions were stopped by adding 100 μl of 0.2 N HCl to each vial, followed by 3,000 μl of toluene/ethyl acetate (2:1 by vol.) containing Omnifluor, 4 g/liter. The vials were capped and their contents mixed by 20 inversions/vial. Radioactivity was measured by liquid scintillation counting. Radioactivity of the quantity of substrate used per vial was measured by adding 100 μl of substrate to 10 ml. of RIAfluor in a 20 ml. scintillation vial.

Enzymic activity was computed in terms of percent substrate utilization:

$$[E] = \frac{T - B}{S_o} \times 100$$

Results, expressed in terms of the substrate utilization of the control reaction mixture (enzyme plus substrate, no inhibitor), are shown below:

| Final Concentration of Inhibitor | Percent Substrate Utilization | Percent Inhibition |
|---|---|---|
| 0 (control) | 8.17 | 0 |
| 5.1 × 10⁻⁴M | 0 | 100% |
| 4.7 × 10⁻⁵M | 0 | 100 |
| 4.2 × 10⁻⁶M | 0.16 | 98 |
| 3.9 × 10⁻⁷M | 0.65 | 92 |
| 3.5 × 10⁻⁸M | 3.51 | 57 |
| 3.2 × 10⁻⁹M | 7.27 | 11 |
| 2.9 × 10⁻¹⁰M | 8.16 | 0 |
| 2.6 × 10⁻¹¹M | 8.19 | 0 |
| 2.4 × 10⁻¹²M | 8.19 | 0 |

By inspection of the column Percent Inhibition, it is evident that the $I_{50}$ of the inhibitor is approximately $3.5 \times 10^{-8}$ M. The $I_{50}$ is defined as that concentration of inhibitor required to reduce enzyme activity by 50%.

EXAMPLE 5

Assays of human serum angiotensin converting enzyme using [³H]Hippuryl-Gly-Gly and [³H]hippuryl-His-Leu as substrates Thirty one human serum samples were assayed for their angiotensin converting enzyme activities. In the first instance, 100 μl of a given serum sample was diluted with 400 μl of 0.05 M Hepes buffer, pH 8.0, containing 0.1 M NaCl and 0.6 M Na₂SO₄ (the 1:5 dilution). A sample, 100 μl, of the 1:5 dilution was then mixed with 700 μl of 0.05 M Hepes buffer, pH 8.0, containing 0.1 M NaCl and 0.75 M Na₂SO₄ (the 1:40 dilution).

For the assay using [³H]hippuryl-Gly-Gly as substrate, 100 μl of the 1:5 dilution was added to a 7 ml. mini-vial and then 100 μl of the substrate (230,000 c.p.m., 16 mM) in the first described buffer was added (test vials, T). A blank (B) was composed of 100 μl of buffer plus 100 μl of buffered substrate. The vials were incubated at 37° C. for 30 minutes, then 100 μl of 0.5 N HCl was added, and followed by 4.0 ml. of toluene/ethyl acetate (2:1 by vol.) containing Omnifluor, 4 g/liter. The vials were capped, mixed by inversion and then submitted to liquid scintillation counting. Total radioactivity of the substrate of the reaction mixture (S) was measured by counting a mixture of 100 μl of the buffered substrate plus 10 ml. of RIAfluor in a 20 ml. scintillation vial.

For the assay using [³H]hippuryl-His-Leu as substrate, 100 μl of the 1:40 dilution of a given serum sample was added to a 7 ml. mini-vial and then 100 μl of buffered substrate, 220,000 c.p.m., 80 nM (buffer: 0.05 M Hepes, pH 8.0, plus 0.1 M NaCl and 0.75 M Na₂SO₄) was added. The reaction mixture was incubated at 37° C. for 15 minutes. The reaction was stopped and extraction effected as described above. Results are shown below: Computation for the [³H]hippuryl-Gly-Gly assay:

$$[E]/\text{ml.} = \frac{\frac{T - B}{S_o} \times 1600 \text{ nmoles}}{30 \text{ min.} \times 0.02 \text{ ml.}}$$

where [E]/ml. is milliunits of enzyme activity/ml. of undiluted serum. One milliunit is that quantity of ACE required to hydrolyze substrate at a rate of 1 nmol/min. at 37° C. T=c.p.m. of a given test vial, B=c.p.m. of a blank vial, and $S_o$=c.p.m. of substrate used in each vial. The term 1600 nmoles indicates the quantity of substrate in each vial; 30 minutes is the time of incubation and 0.02 ml. is the quantity of undiluted serum in a given test vial.

Computation for the [³H]hippuryl-His-Leu assay:

$$[E]/\text{ml.} = \frac{\frac{T - B}{S_o} \times 100}{15 \text{ min.} \times 0.0025 \text{ ml.}}$$

T, B and $S_o$ are as defined above; the term 100 converts fractional substrate utilization into percentage; 15 minutes is the time of incubation; and 0.0025 ml. is the volume of undiluted serum in a given test vial. [E] is defined in terms of kinetic first order reaction units: 1 unit is the quantity of enzyme required to hydrolyze substrate at 1% per minute at 37° C.

| Serum Sample | X<br>HGG<br>minivial | Y<br>HHL<br>minivial |
|---|---|---|
| 1 | 130.0 | 146.2 |
| 2 | 126.9 | 140.7 |
| 3 | 127.6 | 147.8 |
| 4 | 113.4 | 132.6 |
| 5 | 123.3 | 141.0 |
| 6 | 136.2 | 149.3 |

-continued

| Serum Sample | X HGG minivial | Y HHL minivial |
|---|---|---|
| 7 | 131.0 | 150.1 |
| 8 | 132.5 | 152.7 |
| 9 | 125.2 | 147.4 |
| 10 | 133.0 | 152.2 |
| 11 | 141.9 | 175.4 |
| 12 | 144.9 | 179.5 |
| 13 | 140.8 | 171.2 |
| 14 | 147.1 | 177.8 |
| 15 | 144.4 | 168.2 |
| 16 | 129.7 | 162.1 |
| 17 | 151.3 | 196.7 |
| 18 | 122.8 | 160.3 |
| 19 | 152.2 | 204.3 |
| 20 | 154.9 | 194.4 |
| 21 | 136.0 | 174.9 |
| 22 | 103.7 | 138.3 |
| 23 | 96.4 | 124.1 |
| 24 | 102.4 | 140.2 |
| 25 | 117.2 | 143.2 |
| 26 | 130.4 | 158.6 |
| 27 | 172.3 | 253.2 |
| 28 | 164.3 | 221.3 |
| 29 | 105.6 | 143.5 |
| 30 | 71.7 | 119.4 |
| 31 | 77.3 | 112.9 |

Correlation of assays:
r=0.89
y=mx+b
m=1.1765, b=9.336

EXAMPLE 6

Assay of trypsin using (D)Phe-Pro-Arg-[$^3$H]benzylamide as substrate in a modified mini-vial procedure Comment: For reasons not clearly understood, many of the [$^3$H]benzylamide-containing substrates cannot be used in the mini-vial procedure described in Example 2. As an example of the problem, (D)Phe-Pro-Arg-[$^3$H]benzylamide can be incubated with buffer in a small volume (e.g., 100 μl) in a 7 ml. minivial. To this solution is added excess NaOH (e.g., 200 μl of 0.1 N NaOH) and then 10 vol. (3,000 μl) of toluene containing Omnifluor (4 g/l), is mixed with the alkaline aqueous solution. After phase separation, the vial is submitted to liquid scintillation counting and the measured c.p.m. are compared to the total c.p.m. of the amount of substrate used. Ideally, the comparison would indicate the quantity of substrate extracted into toluene. However, the c.p.m. observed may exceed 40% of the radioactivity of substrate and then rise with time to greater than 80%. At any time following phase separation (up to 24 hours), a sample of the toluene phase can be transferred to another scintillation vial and the toluene extractable $^3$H is seen to be less than 3% of the total substrate used. The latter observation indicates that alkaline hydrolysis of the substrate does not contribute to the extractability of $^3$H into toluene and further shows that the true relative solubility of substrate in toluene is extremely low. As a practical matter, the observation also indicates that by transferring a known fraction of the organic phase to a new vial, the true extractability of $^3$H can be assessed. Thus by comparing toluene extractable $^3$H of substrate-containing reaction mixtures incubated with and without enzyme (e.g., trypsin), enzymecatalyzed release of [$^3$H]benzylamine can be assessed.

To illustrate this "modified minivial" procedure,

A. The substrate, (D)Phe-Pro-Arg-[$^3$H]benzylamide, was dissolved in 0.2 M Tris-HCl buffer, pH 7.75, plus 0.15 M NaCl to a final concentration of 120,000 c.p.m./50 μl (approximately 40 nM). Separately, trypsin (222 units/mg) was diluted serially in buffer to give a series of dilutions ranging from 2 units/ml. to 0.0312 units/ml. Separate reaction mixtures were composed by adding, to 7 ml. scintillation vials, 50 μl of buffered substrate plus 50 μl of buffer (blank) or a trypsin dilution (test). The reaction mixtures were incubated at 37° C. for 10 minutes and then 1.0 ml. of 0.1 N NaOH was added to each. Toluene, containing Omnifluor (4 g/liter), was added at 1 ml. per vial. The vials were capped and the contents of each were mixed by 30 inversions. The caps were removed, and the solvent phases allowed to separate spontaneously. After phase separation, 0.5 ml. of a given toluene phase was transferred to a 2 ml. scintillation vial. The 2 ml. vials were capped and then submitted to liquid scintillation counting. The results were computed in terms of percentage utilization of substrate (corrected for relative solubilities of substrate and benzylamine) and are shown below.

| Trypsin (units/ml. of final reaction mixture) | Substrate Utilization (%) |
|---|---|
| 0 | 0 |
| 0.0156 | 3.54 |
| 0.0312 | 6.03 |
| 0.0625 | 11.96 |
| 0.125 | 21.64 |
| 0.25 | 40.76 |
| 0.5 | 67.21 |
| 1.0 (4.5 ug/ml.) | 96.11 |

From these data, it is evident that, over the entire range of trypsin concentrations used, the reaction obeyed first order enzyme kinetics. Clearly, the sensitivity of the assay is such that less than 0.0156 units of trypsin/ml. can be measured. The sensitivity can be increased by extending the length of the incubation and/or by adding calcium to the assay buffer.

B. A similar assay is performed by conducting the incubation step in a 12×75 mm test tube. The reaction is stopped by adding base. The extraction step is accomplished by adding toluene containing Omnifluor and partitioning via vortex mixing. After phase separation, a fraction (usually half) of the toluene phase is transferred to a 2 ml. scintillation vial and radioactivity measured as before with similar results.

C. The transfer of the organic phase, containing a scintillator such as Omnifluor, can be accomplished such that the disposable pipette tip used for transfer becomes the scintillation vial. In a modification of A. or B. above, 100 μl of the upper phase is drawn into a Eppendorf pipette tip. The outlet of the tip is sealed by a method such as clamping or by pressing the outlet into moist clay. The tip is then removed from the pipetting apparatus and placed in a 7 ml. scintillation vial. The radioactivity of the contents of the sealed pipette tip is submitted for liquid scintillation counting. The 7 ml. scintillation vial is not contaminated with radioactivity and can be used repeatedly.

I claim:

1. A method for the detection of enzymic activity in biological material by an assay procedure comprising the steps of:
   mixing a radiolabelled substrate for the enzyme with the biological material in a vial of no more than 20 ml. volume under conditions where the enzyme to be detected is catalytically active if present in the substrate, incubating the biological material—substrate mixture in said vial to permit the enzyme if present to catalyze the hydrolysis of the substrate, stopping the hydrolysis by adding to said vial an agent effective for that purpose, mixing in said vial the incubated material containing the hydrolyzed substrate from the preceding step with at least one organic solvent for a radiolabelled hydrolysis remnant product of the substrate that does not dissolve the substrate which also contains a scintillant in sufficient quantity to permit measurement, permitting the mixture in said vial to separate on its own, without centrifugation into an aqueous phase containing unreacted substrate and an organic phase containing radiolabelled remnant product, and measuring the radioactivity of the radiolabelled remnant product in the organic phase.

2. The method of claim 1 wherein the radioactivity measurement is carried out upon the organic phase in the same vial used for the preceding steps.

3. The method of claim 1 wherein a measured amount of organic phase is withdrawn from the vial and subjected to radioactivity measurement in another vessel.

4. The method of claim 2 wherein the reaction vial has a volume of 7 ml. or less.

5. The method of claim 2 wherein the enzyme is angiotensin converting enzyme, the substrate is a radiolabelled derivative selected from the group consisting of HipHisLeu, HipGlyGly, and benzoyl GlyHisLeu, the reaction is stopped with aqueous HCl and the organic solvent is a mixture of ethyl acetate and toluene in 1:2 volume ratio.

6. The method of claim 1, 2 or 4 wherein the enzyme is aminopeptidase A, the substrate is the tritiated benzylamide of aspartic acid, the reaction is stopped with aqueous sodium hydroxide and the organic solvent is ethyl acetate:toluene in 1:2 volume ratio.

7. The method of claim 1, 2 or 4 wherein the enzyme is a carboxypeptidase, the substrate is tritiated benzoyl PheArg, the reaction is stopped with aqueous HCl and the organic solvent is toluene.

8. The method of claim 1 or 3 wherein the enzyme is trypsin, the substrate is (D)Phe-Pro-Arg tritiated benzylamide, the reaction is stopped with aqueous NaOH and the organic solvent is toluene.

9. The method of claim 5 wherein the substrate is labelled with tritium.

10. The method of claim 5 wherein the substrate is labelled with $^{14}C$.

11. The method of claim 5 wherein the substrate is labelled with $^{125}I$ or $^{131}I$.

12. The method of claim 1, 2 or 4 wherein the enzyme is any enzyme capable of cleaving a substrate hydrolytically and the substrate is so designed that upon hydrolysis it will produce a radiolabelled remnant product that can be selectively extracted from aqueous solution with a water immiscible organic solvent compatible with the scintillant.

13. The method of claim 2 in which the enzyme is angiotensin converting enzyme, the sample contains no carboxypeptidases, the substrate is a radiolabelled benzoyl Pro-Phe-Arg, the reaction is stopped with aqueous HCl and the organic solvent is a 1:2 mixture by volume of ethyl acetate:toluene.

14. The method of claim 13 in which the radiolabel is tritium, $^{14}C$ or radioactive iodine.

15. The method of claim 5 wherein the reaction vial has a volume of 7 ml or less.

16. The method of claim 13 wherein the reaction vial has a volume of 7 ml or less.

17. The method of any of claims 1, 2, 3, 4, 9, 10, 11, 13, 16 or 15 in which the reaction vessel is a Beem capsule.

18. The method of claim 5 in which the reaction vessel is a Beem capsule.

19. The method of claim 6 in which the reaction vessel is a Beem capsule.

20. The method of claim 7 in which the reaction vessel is a Beem capsule.

21. The method of claim 8 in which the reaction vessel is a Beem capsule.

22. The method of claim 12 in which the reaction vessel is a Beem capsule.

23. The method of claim 14 in which the reaction vessel is a Beem capsule.

* * * * *

UNITED STATES PATENT AND TRADEMARK OFFICE
CERTIFICATE OF CORRECTION

PATENT NO. : 4,372,941
DATED : 2/8/83
INVENTOR(S) : James W. Ryan

It is certified that error appears in the above-identified patent and that said Letters Patent is hereby corrected as shown below:

Claim 17 should be corrected to read --

"The method of any of claims 1, 2, 3, 4, 9, 10, 11, 13, 15 or 16 in which the reaction vessel is a Beem capsule".

Signed and Sealed this

Tenth Day of January 1984

[SEAL]

Attest:

GERALD J. MOSSINGHOFF

*Attesting Officer*　　*Commissioner of Patents and Trademarks*